(12) United States Patent
Jalgaonkar et al.

(10) Patent No.: US 11,452,841 B2
(45) Date of Patent: Sep. 27, 2022

(54) ASPIRATION CATHETER SYSTEM

(71) Applicant: Covidien LP, Mansfield, MA (US)

(72) Inventors: Ujwal Jalgaonkar, Irvine, CA (US);
Edwin Bon, Lake Elsinore, CA (US);
Peter Skujins, Laguna Hills, CA (US);
Eric Mintz, Costa Mesa, CA (US)

(73) Assignee: COVIDIEN LP, Mansfield, MA (US)

(*) Notice: Subject to any disclaimer, the term of this patent is extended or adjusted under 35 U.S.C. 154(b) by 167 days.

(21) Appl. No.: 16/381,642

(22) Filed: Apr. 11, 2019

(65) Prior Publication Data

US 2020/0324079 A1 Oct. 15, 2020

(51) Int. Cl.
*A61M 25/00* (2006.01)
*A61M 1/00* (2006.01)

(52) U.S. Cl.
CPC .......... *A61M 25/0029* (2013.01); *A61M 1/84* (2021.05); *A61M 25/003* (2013.01);
(Continued)

(58) Field of Classification Search
CPC .............. A61M 25/0029; A61M 1/008; A61M 25/003; A61M 25/0043; A61M 2025/0039; A61M 2025/0175; A61M 2025/0006; A61M 2025/006; A61M 25/007; A61M 25/00; A61M 25/0075; A61M 2025/0078; A61M 2025/0004; A61M 2025/0008;
(Continued)

(56) References Cited

U.S. PATENT DOCUMENTS 3,945,385 A   3/1976   Sackner
3,965,901 A   6/1976   Penny et al.
(Continued)

FOREIGN PATENT DOCUMENTS

EP   2656869 A1      10/2013
WO   2003082377 A1   10/2003
WO   2006132434 A1   12/2006

OTHER PUBLICATIONS

International Search Report and Written Opinion issued in International Application No. PCT/US2020/024480, dated Jul. 14, 2020 15 pp.

(Continued)

*Primary Examiner* — Bradley J Osinski
(74) *Attorney, Agent, or Firm* — Shumaker & Sieffert, P.A.

(57) ABSTRACT

In some examples, an aspiration catheter system includes an outer catheter and an inner catheter configured to be positioned within the outer catheter lumen, and an alignment element. The outer catheter defines an outer catheter lumen and an outer catheter distal opening. The inner catheter defines an inner catheter lumen, an inner catheter distal opening, and a plurality of sidewall openings proximal to the inner catheter distal opening. The alignment element is configured to indicate a predetermined position of the inner catheter relative to the outer catheter when the inner catheter is received within the outer catheter distal opening. When the inner catheter is at the predetermined position, at least one sidewall opening of the plurality of sidewall openings remains positioned within the outer catheter lumen and at least one other sidewall opening of the plurality of sidewall openings is positioned distal to the outer catheter distal opening.

23 Claims, 4 Drawing Sheets

(52) U.S. Cl.
CPC ... *A61M 25/0043* (2013.01); *A61B 2217/005* (2013.01); *A61M 2025/0039* (2013.01)

(58) Field of Classification Search
CPC .... A61M 1/84; A61B 2217/005; A61B 17/22; A61B 17/32037; A61F 2/013; A61F 9/007; A61F 9/00736; A61F 9/00745
See application file for complete search history.

(56) References Cited

U.S. PATENT DOCUMENTS

| | | | |
|---|---|---|---|
| 5,147,332 A | | 9/1992 | Moorehead |
| 5,180,364 A | | 1/1993 | Ginsburg |
| 5,224,938 A | * | 7/1993 | Fenton, Jr. ........ A61M 25/0075 604/9 |
| 5,248,297 A | * | 9/1993 | Takase ................ A61M 1/0047 604/22 |
| 5,505,710 A | * | 4/1996 | Dorsey, III ............. A61M 1/84 604/164.11 |
| 5,562,612 A | * | 10/1996 | Fox .................... A61F 9/00736 604/22 |
| 6,398,754 B1 | * | 6/2002 | Sutton ................ A61F 9/00745 604/22 |
| 6,849,068 B1 | | 2/2005 | Bagaoisan et al. |
| 7,491,192 B2 | | 2/2009 | DiFiore |
| 7,763,010 B2 | | 7/2010 | Evans et al. |
| 8,409,237 B2 | | 4/2013 | Galdonik et al. |
| 8,453,648 B2 | | 6/2013 | Black et al. |
| 9,445,831 B2 | | 9/2016 | Mark |
| 2007/0060888 A1 | | 3/2007 | Goff et al. |
| 2009/0157002 A1 | | 6/2009 | Dumot et al. |
| 2010/0152706 A1 | | 6/2010 | Morris et al. |
| 2010/0204712 A1 | * | 8/2010 | Mallaby ........... A61B 17/32037 606/128 |
| 2013/0144205 A1 | | 6/2013 | Brandeis |
| 2015/0065951 A1 | | 3/2015 | Freyman et al. |
| 2015/0088051 A1 | * | 3/2015 | Ragg ..................... A61K 47/32 514/723 |
| 2018/0042623 A1 | | 2/2018 | Batiste |
| 2018/0098778 A1 | | 4/2018 | Ogle |

OTHER PUBLICATIONS

International Preliminary Report on Patentability from International Application No. PCT/US2020/024480, dated Sep. 28, 2021, 8 pp.

* cited by examiner

ASPIRATION CATHETER SYSTEM

TECHNICAL FIELD

This disclosure relates to medical aspiration.

BACKGROUND

A medical catheter defining at least one lumen has been proposed for use with various medical procedures. For example, in some cases, a medical catheter may be used to access and treat defects in blood vessels, such as, but not limited to, lesions or occlusions in blood vessels. This treatment may involve drawing fluid through the medical catheter.

SUMMARY

In some aspects, this disclosure describes example aspiration catheter systems configured to provide suction from and continuous flow of fluid through an aspiration catheter even when a distal opening of the aspiration catheter is blocked by a tissue. Aspiration catheter systems include an inner catheter with sidewall openings that allow fluid to flow into a lumen of the inner catheter when a distal opening of the inner catheter is blocked by the tissue. An outer catheter surrounding the inner catheter provides a flow path for aspiration fluid to a site of the tissue and through the sidewall openings of the inner catheter, ensuring continuous flow into the lumen of the inner catheter for removing any portions of the tissue that may come loose. A clinician can adjust the position of the inner catheter relative to the outer catheter to achieve a desired flow characteristic. In this way, a clinician may more effectively remove the tissue from vasculature of the patient when compared to aspiration catheters that provide reduced or no flow during engagement of a tissue.

In some examples, an aspiration catheter system includes an outer catheter and an inner catheter configured to be positioned within the outer catheter lumen, and an alignment element. The outer catheter defines an outer catheter lumen and an outer catheter distal opening. The inner catheter defines an inner catheter lumen, an inner catheter distal opening, and a plurality of sidewall openings proximal to the inner catheter distal opening. The alignment element is configured to indicate a predetermined position of the inner catheter relative to the outer catheter when the inner catheter is received within the outer catheter distal opening. When the inner catheter is at the predetermined position, at least one sidewall opening of the plurality of sidewall openings remains positioned within the outer catheter lumen and at least one other sidewall opening of the plurality of sidewall openings is positioned distal to the outer catheter distal opening.

Clause 1: In one example, an aspiration catheter system comprises an outer catheter defining an outer catheter lumen and an outer catheter distal opening; an inner catheter configured to be positioned within the outer catheter lumen, the inner catheter defining an inner catheter lumen, an inner catheter distal opening, and a plurality of sidewall openings proximal to the inner catheter distal opening; and an alignment element configured to indicate a predetermined position of the inner catheter relative to the outer catheter when the inner catheter is received within the outer catheter distal opening, wherein when the inner catheter is at the predetermined position, at least one sidewall opening of the plurality of sidewall openings remains positioned within the outer catheter lumen and at least one other sidewall opening of the plurality of sidewall openings is positioned distal to the outer catheter distal opening.

Clause 2: In some examples of the aspiration catheter system of clause 1, the alignment element comprises a visible marker on the inner catheter.

Clause 3: In some examples of the aspiration catheter system of clause 1 or clause 2, the alignment element comprises an alignment structure extending from the inner catheter and is configured to engage with a proximal end of the outer catheter.

Clause 4: In some examples of the aspiration catheter system any of clauses 1-3, the alignment element comprises a plurality of markers, each marker corresponding to a predetermined position of at least one sidewall opening of the plurality of sidewall openings of the inner catheter relative to the outer catheter distal opening.

Clause 5: In some examples of the aspiration catheter system any of clauses 1-4, an inner circumference of the outer catheter is between about 50 microns and about 200 microns greater than an outer circumference of the inner catheter.

Clause 6: In some examples of the aspiration catheter system any of clauses 1-5, at least one sidewall opening of the plurality of sidewall openings comprises a one-way valve configured to permit flow of fluid into the inner catheter lumen.

Clause 7: In some examples of the aspiration catheter system of clause 6, the one-way valve is configured to open in response to a differential pressure between the outer catheter lumen and the inner catheter lumen being greater than or equal to a predetermined threshold value.

Clause 8: In some examples of the aspiration catheter system of clause 6, the one-way valve comprises a duckbill valve, a slit valve, or a flexible flap positioned at the respective sidewall openings.

Clause 9: In some examples of the aspiration catheter system any of clauses 1-8, the distal-most sidewall opening of the plurality of sidewall openings is positioned between about 0.5 centimeters and about 10 centimeters proximal to the inner catheter distal opening.

Clause 10: In some examples of the aspiration catheter system any of clauses 1-9, the catheter system further comprises a fluid circulation system coupled to a proximal portion of the outer catheter and a proximal portion of the inner catheter, wherein the fluid circulation system is configured to deliver fluid through the outer catheter lumen and receive fluid through the inner catheter lumen.

Clause 11: In some examples of the aspiration catheter system of clause 10, the fluid comprises saline.

Clause 12: In some examples of the aspiration catheter system any of clauses 1-11, the sidewall openings of the plurality of sidewall openings are circumferentially distributed around an outer perimeter of the inner catheter.

Clause 13: In some examples of the aspiration catheter system any of clauses 1-12, the sidewall openings of the plurality of sidewall openings are distributed axially along the inner catheter.

Clause 14: In some examples, a method comprises: introducing at least a portion of an outer catheter and an inner catheter of an aspiration catheter system into vasculature of a patient, the aspiration catheter system comprising: the outer catheter defining an outer catheter lumen and an outer catheter distal opening; the inner catheter defining an inner catheter lumen, an inner catheter distal opening, and a plurality of sidewall openings proximal to the inner catheter distal opening; and an alignment element configured to indicate a predetermined position of the inner catheter relative to the outer catheter when the inner catheter is received within the outer catheter distal opening. In these examples, the method further comprises positioning the inner catheter within the outer catheter lumen at the predetermined position such that at least one sidewall opening of the plurality of sidewall openings remains positioned within the outer catheter lumen and at least one other sidewall opening of the plurality of sidewall openings is positioned distal to the outer catheter distal opening; and delivering a fluid through the outer catheter lumen and through at least one of: the outer catheter distal opening into the vasculature of the patient, or at least one sidewall opening of the plurality of sidewall openings into the inner catheter lumen.

Clause 15: In some examples of the method of clause 14, the fluid is delivered through the outer catheter lumen through the at least one sidewall opening into the inner catheter lumen in response to a differential pressure between the outer catheter lumen and the inner catheter lumen being greater than or equal to a predetermined threshold value.

Clause 16: In some examples of the method of clause 15 or clause 16, the method further comprises positioning the inner catheter distal opening proximate to a soft tissue in the vasculature; and generating a suction in the inner catheter lumen.

Clause 17: In some examples of the method of clause 16, the inner catheter distal opening is positioned in the vasculature so that the soft tissue substantially covers the inner catheter distal opening, and the fluid is delivered through the at least one sidewall opening in response to the soft tissue substantially covering the inner catheter distal opening.

Clause 18: In some examples of the method of any of clauses 14-17, the alignment element comprises an alignment structure extending from the inner catheter and configured to engage with a proximal end of the outer catheter.

Clause 19: In some examples of the method of any of clauses 14-18, the alignment element comprises a plurality of markings, each marking corresponding to a predetermined position of at least one sidewall opening of the plurality of sidewall openings of the inner catheter relative to the outer catheter distal opening.

Clause 20: In some examples of the method of any of clauses 14-19, the fluid comprises saline.

Clause 21: In some examples, an aspiration catheter system comprises: an outer catheter defining an outer catheter lumen and an outer catheter distal opening; an inner catheter configured to be positioned within the outer catheter lumen, the inner catheter defining an inner catheter lumen, an inner catheter distal opening, and a plurality of sidewall openings proximal to the inner catheter distal opening; and an alignment element configured to indicate a predetermined position of the inner catheter relative to the outer catheter when the inner catheter is received within the outer catheter distal opening, wherein when the inner catheter is at the predetermined position, the aspiration catheter system defines: a first flow path of fluid from the outer catheter lumen through the outer catheter distal opening and the inner catheter distal opening to the inner catheter lumen, a second flow path of the fluid from the outer catheter lumen through the outer catheter distal opening and at least a first sidewall opening of the plurality of sidewall openings to the inner catheter lumen, and a third flow path of the fluid from the outer catheter lumen directly through at least a second sidewall opening of the plurality of sidewall openings to the inner catheter lumen.

Clause 22: In some examples of the system of clause 21, the system further comprises an aspiration pump fluidically coupled to the outer catheter and the inner catheter, the aspiration pump configured to: deliver an aspiration fluid to the outer catheter lumen; generate a positive pressure on the outer catheter lumen; and generate a negative pressure on the inner catheter lumen.

Clause 23: In some examples of the system of clause when the inner catheter distal opening is at least partially blocked, the aspiration catheter system is configured to deliver the fluid from the outer catheter lumen to the inner catheter lumen through at least one of the second flow path or the third flow path.

Clause 24: In some examples, an aspiration catheter system comprises: an outer catheter defining an outer catheter lumen and an outer catheter distal opening; an inner catheter configured to be positioned within the outer catheter lumen, the inner catheter defining an inner catheter lumen, an inner catheter distal opening, and at least one sidewall opening proximal to the inner catheter distal opening; and an alignment element configured to indicate a predetermined position of the inner catheter relative to the outer catheter when the inner catheter is received within the outer catheter distal opening, wherein when the inner catheter is at the predetermined position, the at least one sidewall opening is positioned distal to the outer catheter distal opening.

Clause 25: In some examples, a method comprises introducing at least a portion of an outer catheter and an inner catheter of an aspiration catheter system into vasculature of a patient, the aspiration catheter system comprising: the outer catheter defining an outer catheter lumen and an outer catheter distal opening; the inner catheter defining an inner catheter lumen, an inner catheter distal opening, and at least one sidewall opening proximal to the inner catheter distal opening; and an alignment element configured to indicate a predetermined position of the inner catheter relative to the outer catheter when the inner catheter is received within the outer catheter distal opening. In some of these examples, the method further comprises positioning the inner catheter within the outer catheter lumen at the predetermined position such that the at least one sidewall opening is positioned distal to the outer catheter distal opening; and delivering a fluid through the outer catheter lumen and through at least one of: the outer catheter distal opening into the vasculature of the patient, or the at least one sidewall opening into the inner catheter lumen.

The examples described herein may be combined in any permutation or combination.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1A:
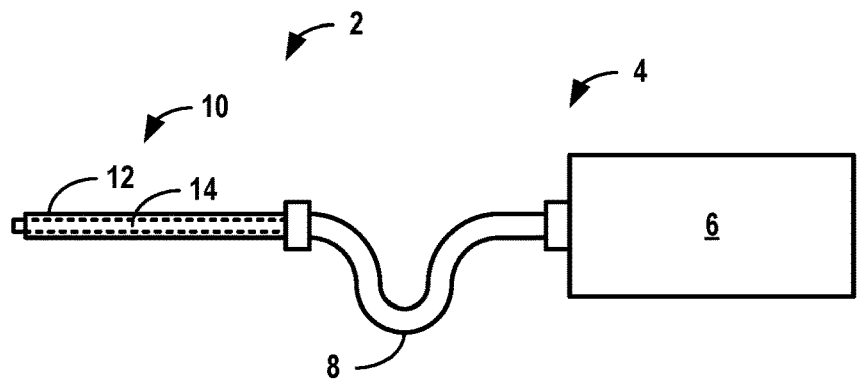
FIG. 1A is a conceptual block diagram illustrating an example aspiration system that includes an aspiration catheter system configured to help maintain suction and continuous flow of fluid on an engaged thrombus.

The disclosure describes aspiration catheter systems, including some examples configured to maintain suction and continuous flow of fluid on an engaged thrombus, as well as aspiration systems including the aspiration catheter system and methods of using the aspiration systems.

Thrombosis occurs when a thrombus (e.g., a blood clot or other embolus) forms and obstructs vasculature of a patient. To treat a patient with thrombosis, a clinician may position an aspiration catheter in a blood vessel of the patient near the thrombus, apply suction to the aspiration catheter, and engage the thrombus with a tip of the aspiration catheter. Once the tip of the aspiration catheter has engaged the thrombus, the clinician may remove the aspiration catheter with the thrombus attached to the tip or suction off pieces of the thrombus through the aspiration catheter until the thrombus is removed from the blood vessel of the patient. The aspiration of the thrombus may be part of an aspiration procedure, such as, but not limited to, a medical procedure using A Direct Aspiration first Pass Technique (ADAPT) for acute stroke thrombectomy, or any other aspiration of thrombus or other material from the neurovasculature or other blood vessels.

During suctioning of the thrombus, the clinician may deliver aspiration fluid to the site of the thrombus and suction fluid through a lumen of the aspiration catheter into a canister located external to the patient. Prior to engagement of the thrombus by the aspiration catheter, this flow and suction of fluid near the thrombus may create turbulence at a surface of the thrombus and remove loose pieces of the thrombus from the surface. However, once the clinician has engaged the thrombus, the thrombus may block the distal opening of the aspiration catheter (e.g., at a tip of the aspiration catheter) and cause a reduction or cessation of flow through the lumen of the aspiration catheter. As a result, the flow of fluid at the surface of the thrombus may be reduced or ceased, and pieces of the thrombus may not be removed as effectively.

In some examples described in this disclosure, an aspiration catheter system may include an outer catheter and an inner catheter positioned within the outer catheter. A space between the inner catheter and the outer catheter enable fluid to be delivered near a distal tip of the aspiration catheter system. The inner catheter includes a plurality of sidewall openings proximal to an inner catheter distal opening. When the inner catheter is at a predetermined position relative to the outer catheter, for example as indicated by an alignment element, at least one sidewall opening is positioned within the outer catheter and at least one other sidewall opening is positioned outside the outer catheter to enable fluid to flow into an inner catheter lumen when an inner catheter distal opening is blocked, such as by the thrombus. In this way, the clinician may maintain both suction on an engaged thrombus and continuous flow of fluid on the engaged thrombus, which may result in more effective removal of the thrombus from the vasculature of the patient.

FIG. 1A is a schematic diagram illustrating an example aspiration system 2 that includes an aspiration catheter system 10 configured to maintain suction and continuous flow of fluid on an engaged thrombus. Aspiration system 2 includes aspiration catheter system 10 and a fluid circulation system 4. Aspiration catheter system 10 includes an outer catheter 12 and an inner catheter 14 positioned in outer catheter 12. Fluid circulation system 4 includes an aspiration pump 6 and aspiration tubing 8. Aspiration tubing 8 is coupled to a proximal portion of outer catheter 12 and a proximal portion of inner catheter 14, such that aspiration pump 6 is in fluidic communication with lumens of both outer catheter 12 and inner catheter 14. While shown as a single unit, aspiration tubing 8 may include a plurality of sections of aspiration tubing, such as a first section of tubing coupled to the proximal portion of outer catheter 12 and a second section of tubing coupled to the proximal portion of inner catheter 14.

Fluid circulation system 4 is configured to deliver fluid from aspiration pump 6 through an outer catheter lumen of outer catheter 12 and receive fluid through an inner catheter lumen of inner catheter 14 into aspiration pump 6. An aspiration fluid, such as saline, may be delivered out of an outer catheter distal opening of outer catheter 12 by positive pressure created by aspiration pump 6, the outer catheter distal opening being an opening to an inner lumen of outer catheter 12. Fluid within vasculature of, such as blood, an aspiration fluid, or a mixture thereof, may be drawn into an inner lumen of the inner catheter via an inner catheter distal opening and/or sidewall opening of inner catheter 14 by negative pressure created by pump 6, the inner catheter distal opening and sidewall opening being openings to the inner lumen of inner catheter 14. The aspiration fluid, e.g., saline, may be selected to be less viscous than blood so that delivery of the aspiration fluid into the vasculature of the patient via outer catheter 12 may help create turbulence in the inner lumen of inner catheter 14 as the aspiration fluid is aspirated through the inner lumen of the inner catheter.

Aspiration catheter system 10 may be configured to be advanced through vasculature of a patient via a pushing force applied to a proximal portion of aspiration catheter system 10 with minimal or no buckling, kinking, or otherwise undesirably deforming (e.g., ovalization). Aspiration catheter system 10 may be used to remove a thrombus, such as a clot or other material such as plaques or foreign bodies, from vasculature of a patient. In such examples, a positive pressure may be applied, such as by aspiration pump 6, to the proximal end of outer catheter 12 to deliver aspiration fluid to the site of the thrombus and a negative pressure may be applied, such as by aspiration pump 6, to the proximal end of inner catheter 14 to draw a thrombus into the inner lumen of inner catheter 14 through one or more distal openings. Aspiration catheter system 10 may be used in various medical procedures, such as a medical procedure to treat an ischemic insult, which may occur due to occlusion of a blood vessel (arterial or venous) that deprives brain tissue, heart tissue or other tissues of oxygen-carrying blood.

In some examples, aspiration catheter system 10 is configured to access relatively distal locations in a patient including, for example, the middle cerebral artery (MCA), internal carotid artery (ICA), the Circle of Willis, and tissue sites more distal than the MCA, ICA, and the Circle of Willis. The MCA, as well as other vasculature in the brain or other relatively distal tissue sites (e.g., relative to the vascular access point), may be relatively difficult to reach with a catheter, due at least in part to the tortuous pathway (e.g., comprising relatively sharp twists or turns) through the vasculature to reach these tissue sites. Each of outer catheter 12 and inner catheter 14 may be structurally configured to be relatively flexible, pushable, and relatively kink- and buckle-resistant, so that it may resist buckling when a pushing force is applied to a relatively proximal section of a respective outer catheter 12 and inner catheter 14 to advance aspiration catheter system 10 distally through vasculature, and so that it may resist kinking when traversing around a tight turn in the vasculature. In some examples, outer catheter 12 may be a guide catheter that is introduced into the vasculature before inner catheter 14, and may define a pathway through which inner catheter 14 may be navigated to a target treatment site.

In some examples, aspiration catheter system 10 is configured to substantially conform to the curvature of the vasculature. In addition, in some examples, aspiration catheter system 10 may have a column strength and flexibility that allows at least the distal portion of aspiration catheter system 10 to be navigated from a femoral artery, through the aorta of the patient, and into the intracranial vascular system of the patient, e.g., to reach a relatively distal treatment site. Alternatively, the elongated body can have a column strength (and/or be otherwise configured) to allow the distal portion of the elongated body to be navigated from a radial artery, through the aorta of the patient or otherwise to a common carotid or vertebral artery, and into the intracranial vascular system of the patient, e.g., to reach a relatively distal treatment site.

Although primarily described as being used to reach relatively distal vasculature sites, aspiration catheter system 10 may also be configured to be used with other target tissue sites. For example, aspiration catheter system 10 may be used to access tissue sites throughout the coronary and peripheral vasculature, the gastrointestinal tract, the urethra, ureters, fallopian tubes, veins and other body lumens.

In some examples, aspiration catheter system 10 may be described in terms of the working length of an elongated body of outer catheter 12 and/or inner catheter 14. The working length of aspiration catheter system 10 may depend on the location of the target tissue site within the body of a patient or may depend on the medical procedure for which aspiration catheter system 10 is used. For example, if aspiration catheter system 10 is a distal access catheter system used to access vasculature in a brain of a patient from a femoral artery access point at the groin of the patient, the elongated body of outer catheter 12 and/or inner catheter 14 may have a working length of about 115 centimeters (cm) to about 145 cm or more, such as about 130 cm, although other lengths may be used. The distal portion may be about 5 cm to about 35 cm in length. The proximal portion may be about 90 cm to about 130 cm in length, depending on the length of the distal portion.

In some cases, a clinician may steer aspiration catheter system 10 through the vasculature of a patient by pushing or rotating a hub and/or the proximal portion of outer catheter 12 and/or inner catheter 14 to navigate the distal portion of aspiration catheter system 10 through the vasculature of a patient. The clinician may apply torque to the hub and/or the proximal portion of outer catheter 12 and/or inner catheter 14 to rotate the distal portion of the respective outer catheter 12 and inner catheter 14.

Aspiration pump 6 is configured to create a positive pressure (i.e., outflow) on outer catheter 12, e.g., to deliver fluid through an inner lumen of outer catheter 12 into vasculature of a patient. Aspiration pump 6 is also configured to create a negative pressure (i.e., vacuum or suction) on inner catheter 14, e.g., to draw fluid through an inner lumen of inner catheter 14 into a reservoir of aspiration pump 6. For example, aspiration pump 6 may include one or more ports configured to couple to aspiration tubing 8, such that the positive or negative pressure created by aspiration pump 6 may be applied to the respective port and through aspiration tubing 8 and other portions of a fluid pathway between aspiration tubing 8 and a respective inner lumen of outer catheter 12 and/or inner lumen of inner catheter 14. A variety of pumps may be used for aspiration pump 6 including, but not limited to, positive displacement pumps, centrifugal pumps, and the like. While illustrated as a single pump, aspiration pump 6 may include a plurality of pump units, such as a first pump for creating the positive pressure and a second pump for creating the negative pressure.

Figure 1B:
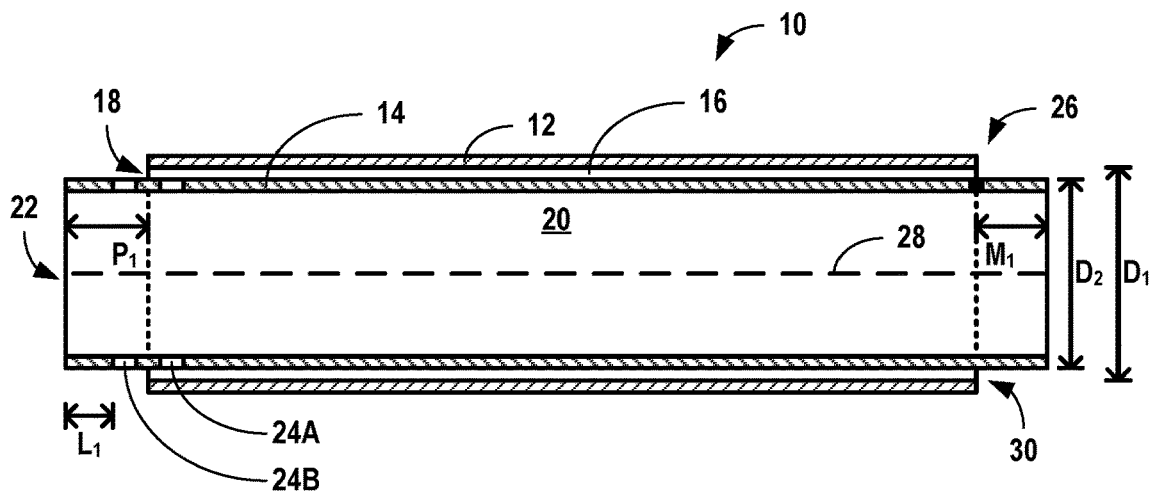
FIG. 1B is a schematic longitudinal cross-sectional diagram illustrating the example aspiration catheter system of FIG. 1A.

FIG. 1B is a schematic diagram illustrating example aspiration catheter system 10 of FIG. 1A. Outer catheter 12 defines an outer catheter lumen 16 and an outer catheter distal opening 18. Outer catheter 12 may include various structural components, such as an inner liner, an outer jacket, and a structural support member, such as a coil and/or or a braid, positioned between at least a portion of the inner liner and at least a portion of the outer jacket.

Outer catheter lumen 16 is configured to transport fluid, such as aspiration fluid, blood, and particulates in the fluid, from a proximal end of outer catheter 12, such as from aspiration pump 6 of FIG. 1A, to a distal end of outer catheter 12, such as outer catheter distal opening 18. Outer catheter lumen 16 may be sized to receive at least a portion of inner catheter 14 while allowing aspiration fluid under a positive pressure provided by an aspiration pump to be delivered to outer catheter opening 18. In some examples, outer catheter 12 may have an inner diameter $D_1$ between or equal to about 0.075 inches (about 1.9 millimeters (mm)) and/or about 0.087 inches (about 2.2 mm), which corresponds to the circumference of outer catheter lumen 16. In some examples, the inner diameter and/or inner circumference of outer catheter lumen 16 may be relatively constant (e.g., constant or nearly constant) from a proximal end of outer catheter 12 to outer catheter opening 18.

Outer catheter distal opening 18 is an opening of outer catheter lumen 16 at a distal end of outer catheter 12. Outer catheter distal opening 18 is configured to receive inner catheter 14, such that at least a portion of inner catheter 14 may be positioned within outer catheter lumen 16. Outer catheter 12 also includes an outer catheter proximal opening 30. Outer catheter proximal opening 30 may be an opening of outer catheter lumen 16 at a proximal end of outer catheter 12. Outer catheter proximal opening may be configured to receive inner catheter 14, such that at least a portion of inner catheter 14 may be positioned outside outer catheter lumen 16. This portion of inner catheter 14 proximal to outer catheter proximal opening 26 may, for example, be used by a clinician to operate a position of inner catheter 14 relative to outer catheter 12. As such, a length of inner catheter 14 may be sufficiently longer than outer catheter 12 to extend past outer catheter distal opening 18 to provide suction and continuous flow into inner catheter lumen 20 and to extend past outer catheter proximal opening 30 to provide a surface for a clinician or other operator to use to operate inner catheter 14 relative to outer catheter 12.

In some examples, one or more portions of an inner surface of outer catheter 12 may be lubricious to facilitate the introduction and passage of inner catheter 14, a therapeutic agent, or the like, through outer catheter lumen 16. Examples of therapeutic agents include, but are not limited to, an oxygenated medium or a pharmaceutical agent, which may be, for example, a vasodilator such as nifedipine or sodium nitroprusside, or a tissue plasminogen activator (t-PA), which can be used to break down blood clots. In some examples, the material from which portions of the inner surface is formed may itself be lubricious (e.g., PTFE). For example, a lubricious inner surface that may allow relatively easy movement of inner catheter 14 and/or fluid through outer catheter lumen 16. In addition to, or instead of, being formed from a lubricious material, in some examples, an inner surface of may be coated with a lubricious coating such as a hydrophilic coating. The inner surface may be formed from any suitable material including, but not limited to, polytetrafluoroethylene (PTFE), expanded PTFE a fluoropolymer, perfluoroalkyoxy alkane (PFA), fluorinated ethylene propylene (FEP), polyolefin elastomer, and the like.

Inner catheter 14 defines an inner catheter lumen 20, an inner catheter distal opening 22, and a plurality of sidewall openings 24A and 24B (collectively "sidewall openings 24") proximal to inner catheter distal opening 22. Inner catheter 14 may include an inner liner, an outer jacket, and a structural support member, such as a coil and/or or a braid, positioned between at least a portion of the inner liner and at least a portion of the outer jacket. Inner catheter 14 may include other structures, such as an expandable member configured to radially expand within a vessel of a patient, e.g., to engage a clot within the vessel.

Inner catheter lumen 20 is configured to transport fluid, such as aspiration fluid, blood, and particulates in the fluid, from a distal end of inner catheter 14, such as from inner catheter distal opening 22 and/or the plurality of sidewall openings 24, to a proximal end of inner catheter 14, such as to aspiration pump 6. Inner catheter 14 may be sized to be housed in outer catheter lumen 16 while still enabling aspiration fluid under a positive pressure provided by an aspiration pump to be delivered to outer catheter opening 18 (in the space between an inner surface of outer catheter 12 and an outer surface of inner catheter 14) and allowing fluid and/or particles from a site of a thrombus to pass through inner catheter lumen 20. In some examples, inner catheter 14 may have an outer diameter $D_2$ between or equal to about 0.050 inches (about 1.3 mm) and/or about 0.074 inches (about 1.9 mm). In some examples, the outer diameter and/or outer circumference of inner catheter 14 may be relatively constant (e.g., constant or nearly constant) from a proximal end of inner catheter 14 to inner catheter opening 22. In other examples, inner catheter 14 may taper in distal direction or otherwise vary in outer diameter along its length.

Inner catheter distal opening 22 is an opening of inner catheter lumen 20 at a distal end of inner catheter 14. In some examples, one or more portions of an inner surface of inner catheter 14 may be lubricious to facilitate the introduction and passage of a medical device, particulates such as pieces of a clot/thrombus, a therapeutic agent, or the like, through inner catheter lumen 20. In some examples, the material from which portions of the inner surface is formed may itself be lubricious (e.g., PTFE). For example, a lubricious inner surface that may allow relatively easy movement of a guidewire, particulates, and/or fluid through inner catheter lumen 20. In addition to, or instead of, being formed from a lubricious material, in some examples, an inner surface of may be coated with a lubricious coating such as a hydrophilic coating. The inner surface may be formed from any suitable material including, but not limited to, polytetrafluoroethylene (PTFE), expanded PTFE a fluoropolymer, perfluoroalkyoxy alkane (PFA), fluorinated ethylene propylene (FEP), polyolefin elastomer, and the like.

In some examples, one or more portions of an inner surface of inner catheter lumen 20 at a distal end of inner catheter 14 may be configured to have a relatively high affinity to a clot material by, for example, using a suitable surface treatment (e.g., a coating and/or etching) on inner liner 18 to promote mechanical or chemical engagement with the clot. (Such affinity may be measured, for example, with a DMA (dynamic mechanical analyzer) equipped with a shear sandwich clamp.) For example, the inner surface of a distal section on inner catheter lumen 20 may be treated with a surface coating, etching, or other roughening mechanism, so that the distal section better engages with the clot, such that the inner surface of the distal section may be configured to promote at least one of mechanical or chemical clot engagement. A roughened or less lubricious surface of an inner surface that is brought in contact with the clot may allow for the clot to stick better to the inner surface, which may allow the clot to be pulled into inner catheter 14 more effectively. Examples of suitable coating materials to increase the affinity of the clot to an inner surface of inner catheter lumen 20 may include, for example, a thermoplastic elastomer such as ChronoPrene™ (AdvanSource Biomaterials, Wilmington, Mass.); a polyolefin elastomer such as ethylene-octene or ethylene-butene copolymer, or the like.

As mentioned above, inner catheter 14 is configured to be positioned within outer catheter lumen 16. As such, an outer diameter or circumference of inner catheter 14 and an inner diameter or circumference of outer catheter lumen 16 may be selected or configured relative to each other. In some examples, an inner circumference of outer catheter 12 may be between about 50 microns and about 400 microns greater than an outer circumference of inner catheter 18.

The plurality of sidewall openings 24 may be configured to flow fluid from at least one of outer catheter lumen 16 and a volume of space (e.g., in a blood vessel) external to outer catheter distal opening 18 into inner catheter lumen 20. Various factors of the sidewall openings 24, such as a number of sidewall openings 24, one or more positions of sidewall openings 24 around and along inner catheter 14, one or more sizes of sidewall openings 24, and the like, may be selected to provide desired and/or predetermined flow characteristics of fluid from outer catheter lumen 16 through outer catheter distal opening 18, from outer catheter lumen 16 into inner catheter lumen 20, and/or from a volume distal to outer catheter distal opening 18 into inner catheter lumen 20.

In some examples, each of the plurality of sidewall openings 24 comprises a one-way valve configured to permit flow of fluid into inner catheter lumen 20. For example, sidewall openings 24 may be configured to allow flow of fluid from outer catheter lumen 16 into inner catheter lumen 20 through sidewall openings 24, such as in response to a positive pressure in outer catheter lumen 16 being greater than a negative pressure in inner catheter lumen 20, but not allow (i.e., no substantial amount of) flow of fluid from inner catheter lumen 20 into outer catheter lumen 16 through sidewall openings 24. The one-way valve can have any suitable configuration. For example, in some examples, the plurality of sidewall openings 24 comprise a duckbill valve, a slit valve, or a flexible flap positioned at one or more (e.g., all) of the sidewall openings of the plurality of sidewall openings. In some examples, the one-way valve does not protrude axially outward from outer catheter 12. For example, the one-way valve may be flush with or below an exterior surface of outer catheter 20. In this way, an exterior surface of outer catheter 20 may be relatively smooth and/or free of protrusions such that the valves may not catch on, for example, the vasculature of the patient or cause unwanted turbulence or flow resistance through outer catheter lumen 16.

In some examples, the plurality of sidewall openings may be configured to open in response to a differential pressure between outer catheter lumen 16 and inner catheter lumen 20 (i.e., a difference between a positive pressure in outer catheter lumen 16 and a negative pressure in inner catheter lumen 20) being greater than or equal to a predetermined differential pressure threshold value. For example, prior to engagement of a thrombus at inner catheter distal opening 22, it may be desired for a majority of aspiration fluid to be delivered through outer catheter distal opening 18 into a volume outside outer catheter distal opening 18 near the thrombus and through inner catheter distal opening 22 from suction in inner catheter lumen 20. However, once the thrombus is engaged with inner catheter 14 and blocking inner catheter distal opening 22, the differential pressure between outer catheter lumen 16 and inner catheter lumen 20 may increase. For example, the thrombus may block flow of aspiration fluid from outer catheter lumen 16 into inner catheter lumen 20, causing an increase in either or both a positive pressure in outer catheter lumen 16 or a negative pressure in inner catheter lumen 20. Once the differential pressure is greater than or equal to the predetermined differential pressure threshold, fluid may flow from outer catheter lumen 16 and/or the volume outside outer catheter distal opening 18 into inner catheter lumen 20.

In some examples, the plurality of sidewall openings 24 may have different differential pressure thresholds. For example, sidewall openings 24 that are more likely to be positioned outside outer catheter distal opening 18 may have a lower differential pressure threshold than sidewall openings that are more likely to be positioned within outer catheter distal opening 18, such that a flow of fluid through sidewall openings closer to the thrombus is higher than flow of fluid further away from the thrombus. The differential pressure threshold for a particular sidewall opening 24 may be selected according to a variety of factors including, but not limited to, expected arterial blood pressure, positive pressure from aspiration pump 6, negative pressure from aspiration pump 6, and the like. For example, the differential pressure may be selected such that the blood pressure in the vessel does not result in flow of fluid into inner catheter lumen 20 via one or more sidewall openings 24.

The plurality of sidewall openings 24 may have a variety of sizes (e.g., diameters, circumferences, lengths, widths, shapes, etc.). In some examples, all sidewall openings of the plurality 24 have substantially the same size (e.g., may only differ by manufacturing variances). In some examples, some sidewall openings of the plurality of sidewall openings 24 have different sizes. In some examples, a size and distribution of the plurality of sidewall openings may be selected according to a particular surface area of a distal end of inner catheter 14. For example, a number of sidewall openings 24 and surface area of each of sidewall openings 24 may be selected so that the plurality of sidewall openings may have a percentage of a surface area of a distal portion (e.g., distal-most 10 centimeters) of inner catheter 14, such as greater than about 10%.

In some examples, sidewall openings 24 may have a median largest surface dimension (e.g., length, width, diameter, or area defined by the boundary of the respective opening) that is less than or equal to about 30% of the diameter of inner catheter lumen 20 in order to help minimize the potential of blocking inner catheter lumen 20 and restricting flow through inner catheter lumen 20. In some examples, sidewall openings 24 may have a median surface area that is less than about that corresponding to a diameter of 0.024 inches (about 0.61 mm). For example, a median surface area may correspond to a flow rate of fluid into inner catheter lumen 20 for a particular positive pressure, negative pressure, position of inner catheter 14 relative to outer catheter 12, such that a median surface area may be selected to balance suction provided at inner catheter distal opening 22 (i.e., near the thrombus) when inner catheter distal opening 22 is not blocked, such that adequate fluid is flowing near the thrombus, with flow through sidewall openings 24 when inner catheter distal opening 22 is blocked, such that adequate fluid is flowing into inner catheter lumen 20. Sidewall openings 24 may also have a minimum size, such as, but not limited to, about 0.001 inches (about 0.025 mm), which may help aid manufacturability of catheter 14. In some examples, the plurality of sidewall openings 24 include between 2 sidewall openings and 15 sidewall openings.

In some examples, the distal-most sidewall opening 24B of the plurality of sidewall openings 24 may be positioned at a length $L_1$ between about 0.5 centimeters and about 10 centimeters proximal to inner catheter distal opening 22. For example, a length $L_1$ greater than about 0.5 centimeters proximal to inner catheter distal opening 22 may correspond to a distance at which the distal-most sidewall opening is unlikely to be plugged (e.g., covered or otherwise blocked) by a thrombus drawn into inner catheter lumen 20. As another example, a length $L_1$ less than about 10 centimeters proximal to inner catheter distal opening 22 may correspond to a distance at which fluid flowing through sidewall openings 24 may have a flow rate or position adequate (e.g., maximum residence time, minimum Reynolds number, minimum flow rate, etc.) for providing suction, circulation, and/or turbulence to a volume within inner catheter lumen 20 near inner catheter distal opening 22.

In some examples, the plurality of sidewall openings may be distributed axially along inner catheter 14 (i.e., along a longitudinal axis 28 of catheter 14). For example, as shown in FIG. 1B, distal-most sidewall opening 24B is distal to proximal-most sidewall opening 24A. While only two axially-distributed sidewall openings are shown, inner catheter 24 may include more than two axially-distributed sidewall openings, such as three, four, five or more axially distributed sidewall openings. In some examples, a size of sidewall openings may vary according to an axial distribution. For example, a size of sidewall openings may increase or decrease along a distal direction.

Figure 1C:
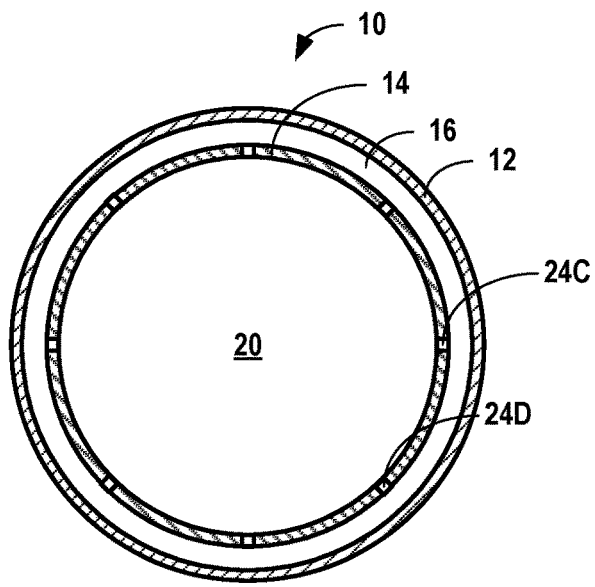
FIG. 1C is a schematic axial cross-sectional diagram illustrating the example aspiration catheter system of FIG. 1A.

In some examples, the plurality of sidewall openings may be distributed around the outer perimeter of inner catheter 14, e.g., circumferentially distributed in the case of inner catheter 14 having a circular cross-section (the cross-section being take in a direction orthogonal to the longitudinal axis of inner catheter 14). FIG. 1C is a schematic axial cross-sectional diagram illustrating example aspiration catheter system 10 of FIG. 1A that includes outer catheter 12 and inner catheter 14. As shown in FIG. 1C, sidewall opening 24C is at a different radial position than sidewall opening 24D. In some examples, a position and/or size of the sidewall openings may be relatively even or constant according to a radial distribution around inner catheter 14. For example, consistency in position and/or size at different radial positions may provide a more even flow of fluid into inner catheter lumen 20. In some examples, a position and/or size of sidewall openings may vary according to a radial distribution around inner catheter 14. For example, variation in sidewall opening sizes at different radial positions may encourage more turbulent flow, as the flow may be less uniform.

Referring back to FIG. 1B, aspiration catheter system 10 can include an alignment element 26. Alignment element 26 can be configured to indicate a predetermined position $P_1$ of inner catheter 14 relative to outer catheter 12 when inner catheter 14 is received within outer catheter inner lumen 16. When inner catheter 14 is at the predetermined position $P_1$, at least one sidewall opening 24A of the plurality of sidewall openings 24 remains positioned within outer catheter lumen 16 and at least one other sidewall opening 24B of the plurality of sidewall openings 24 is positioned distal to outer catheter distal opening 18. This predetermined position $P_1$ may correspond to a configuration that allows both suction and continuous flow through inner catheter lumen 20. While only one predetermined position is shown, in some examples, aspiration catheter system 10 may include a variety of predetermined positions corresponding to various configurations of sidewall openings positioned within outer catheter distal opening 18 and distal to outer catheter distal opening 18. In these examples, alignment element 26 may include a plurality of alignment elements, each alignment element corresponding to a respective predetermined position of inner catheter 14 relative to outer catheter 12.

In some examples, the predetermined position $P_1$ may correspond to various flow paths of fluid from outer catheter lumen 16 to inner catheter lumen 20. For example, when inner catheter 14 is at the predetermined position $P_1$, aspiration catheter system 10 may define (1) a first flow path of fluid from outer catheter lumen 16 through outer catheter distal opening 18 and inner catheter distal opening 22 to inner catheter lumen 20; (2) a second flow path of fluid from outer catheter lumen 16 through outer catheter distal opening 18 and sidewall opening 24B to inner catheter lumen 20; and (3) a third flow path of fluid from outer catheter lumen 16 directly through sidewall opening 24A to inner catheter lumen 20. When inner catheter distal opening 22 may be at least partially blocked, aspiration catheter system 10 may be configured to deliver the fluid from outer catheter lumen 16 to inner catheter lumen 20 through at least one of the second flow path or the third flow path.

Alignment element 26 can be positioned on inner catheter 14, on outer catheter 12, or on both inner catheter 14 and on outer catheter 12. As discussed in further detail below, alignment element 26 may be a visible element, e.g., a visible marker on outer catheter 12 and/or inner catheter 14. In these examples, alignment element 26 may not protrude from a surface of the respective catheter 12, 14, and may be flush (e.g., printed on or embedded in) with the outer surface of the respective catheter 12, 14. In other examples, however, alignment element 26 may include a structure that protrudes from one or both catheters 12, 14, e.g., and engages the other catheter in order to indicate the predetermined position of inner catheter 14 relative to outer catheter 12. As shown in FIG. 1B, alignment element 26 may indicate an alignment position $M_1$ that corresponds to outer catheter proximal opening 30.

Figure 2A:
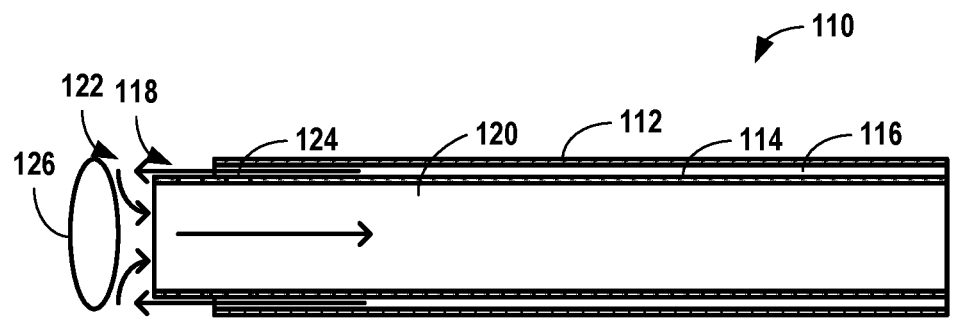
FIG. 2A is a schematic longitudinal cross-sectional diagram illustrating an example aspiration catheter system that includes an outer catheter and an inner catheter positioned near a thrombus prior to engagement of the thrombus.
Figure 2B:
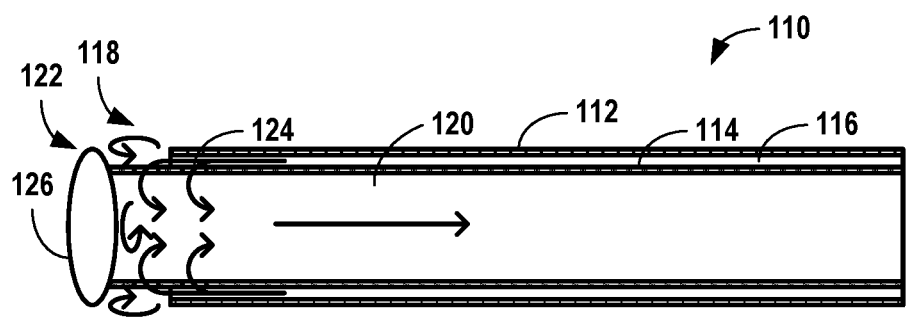
FIG. 2B is a schematic longitudinal cross-sectional diagram illustrating the example aspiration catheter system of FIG. 2A after engagement of the thrombus.

Aspiration catheter systems discussed herein can be configured to maintain suction and continuous flow of fluid on an engaged thrombus. As an illustration, FIGS. 2A and 2B are schematic longitudinal cross-sectional diagrams illustrating an example aspiration catheter system 110 that includes an outer catheter 112 and an inner catheter 114. Aspiration catheter system 110, outer catheter 112, inner catheter 114, an outer catheter lumen 116, an outer catheter distal opening 118, an inner catheter lumen 120, an inner catheter distal opening 122, and a plurality of sidewall openings 124 may correspond to aspiration catheter system 10, outer catheter 12, inner catheter 14, outer catheter lumen 16, outer catheter distal opening 18, inner catheter lumen 20, inner catheter distal opening 22, and plurality of sidewall openings 24 of FIGS. 1A-1C, respectively.

In FIG. 2A, outer catheter 112 and inner catheter 114 are positioned near a thrombus 126 prior to engagement of aspiration catheter system 110 with thrombus 126. When inner catheter distal opening 122 is not blocked by thrombus 126 (or partially blocked by thrombus 126 such that adequate flow of fluid is maintained through inner catheter distal opening 122), an aspiration pump, such as aspiration pump 6, may deliver aspiration fluid through outer catheter lumen 116 between an inner surface of outer catheter 112 and an outer surface of inner catheter 114. The aspiration fluid may be delivered out of outer catheter distal opening 118 into a volume of space outside outer catheter distal opening 18, such as near thrombus 126. In some examples (not shown), the aspiration fluid may be delivered through sidewall openings 124 into inner catheter lumen 120, even when thrombus 126 is not engaged, such as if sidewall openings 124 do not have a differential pressure (i.e., difference between positive pressure and negative pressure) threshold (i.e., minimum differential pressure) or the differential pressure threshold has been reached. The aspiration fluid (or combination of fluids) may flow near a surface of the unengaged or partially engaged thrombus 126, such that pieces of thrombus 126 may be loosened and removed from thrombus 126. Aspiration pump 6 may draw the pieces of thrombus 126, along with fluid, into inner catheter lumen 120. As such, the fluid flow shown in FIG. 2A may characterize a first flow path of fluid from outer catheter lumen 116 through outer catheter distal opening 118 and inner catheter distal opening 122 to inner catheter lumen 120.

FIG. 2B illustrate outer catheter 112 and inner catheter 114 after engagement of thrombus 126. When inner catheter distal opening 122 is blocked by thrombus (or partially blocked by thrombus 126 such that adequate flow of fluid is not maintained through inner catheter distal opening 122), aspiration pump 6 may deliver aspiration fluid through outer catheter lumen 116 between an inner surface of outer catheter 112 and an outer surface of inner catheter 114. However, the aspiration fluid may be delivered through sidewall openings 124 into inner catheter lumen 120, even though inner catheter distal opening 122 is blocked by thrombus 126. For example, aspiration fluid may be delivered from outer catheter inner lumen 116 through a sidewall opening 124 within outer catheter distal opening 116 into inner catheter lumen 120 and/or delivered through outer catheter distal opening 118 into a volume outside outer catheter distal opening 118, such as near thrombus 126, and through a sidewall opening 124 outside outer catheter distal opening 118. In some examples, the aspiration fluid may be delivered through sidewall openings 124 in response to a differential pressure (i.e., difference between positive pressure and negative pressure) exceeding a differential pressure threshold (i.e., minimum differential pressure) of the sidewall openings 124. The aspiration fluid (or combination of fluids) may flow near a surface of the engaged thrombus 126 within inner catheter lumen 120, such that pieces of thrombus 126 may continue to be loosened and removed from thrombus 126. As such, the fluid flow shown in FIG. 2B may characterize a second flow path of fluid from outer catheter lumen 116 through outer catheter distal opening 118 and at least a first sidewall opening of the plurality of sidewall openings 124 to inner catheter lumen 120, and a third flow path of fluid from outer catheter lumen 116 directly through a second sidewall opening of the plurality of sidewall openings 124 to inner catheter lumen 120.

Aspiration pump 6 may draw the pieces of thrombus 126, along with fluid, into inner catheter lumen 120 for removal of the pieces of thrombus 126. In this way, aspiration catheter system 110 may maintain both suction and -partial flow through inner catheter lumen 120 on engaged thrombus 126 to remove thrombus 126, even when distal opening 122 is partially or fully blocked by thrombus 126.

Figures 3A, 3B, 3C:
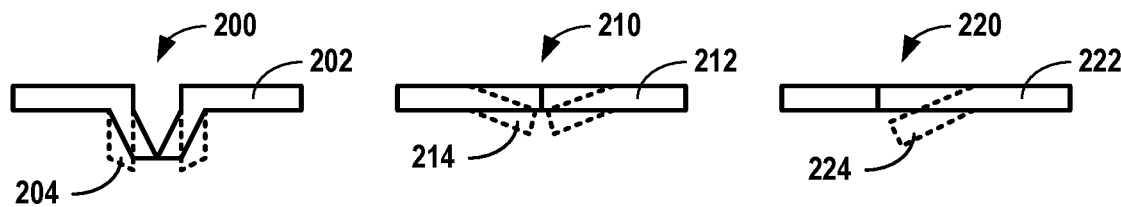
FIG. 3A is a schematic diagram illustrating an example duckbill valve.
FIG. 3B is a schematic diagram illustrating an example slit valve.
FIG. 3C is a schematic diagram illustrating an example flap valve.

In some examples, the sidewall openings discussed herein may include one-way valves having a variety of opening mechanisms. FIGS. 3A-3C are schematic diagrams illustrating various valve configurations for sidewall openings. FIG. 3A is a schematic diagram illustrating an example duckbill valve 200. Duckbill valve 200 may include two or more flaps 204 extending from an inner catheter 202. Duckbill valve 200 may be configured to open in response to a differential pressure threshold being reached or exceeded. FIG. 3B is a schematic diagram illustrating an example slit valve 210. Slit valve 210 may include two or more sides in inner catheter 212. Slit valve 210 may be configured to deform in response to a differential pressure threshold being exceeded. FIG. 3C is a schematic diagram illustrating an example flap valve 220. Flap valve 220 may include one or more flaps 224 extending from inner catheter 222. Flap valve 220 may be configured to open in response to a differential pressure threshold being exceeded and may be aided by a direction of fluid flow past the flaps 224.

Figure 4A:
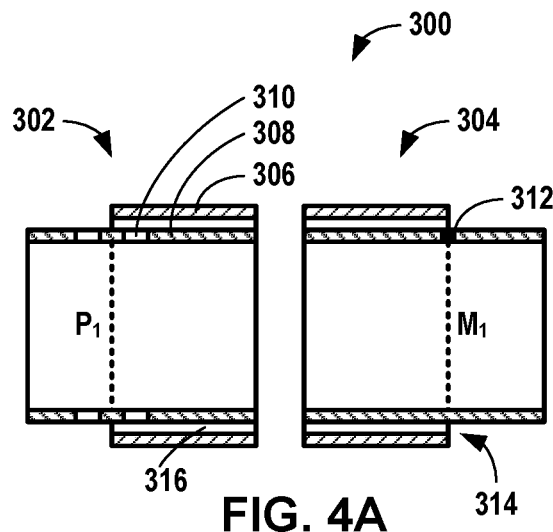
FIG. 4A is a schematic longitudinal cross-sectional diagram illustrating an example aspiration catheter system that includes an alignment element comprising one or more visible markers.
Figure 4B:
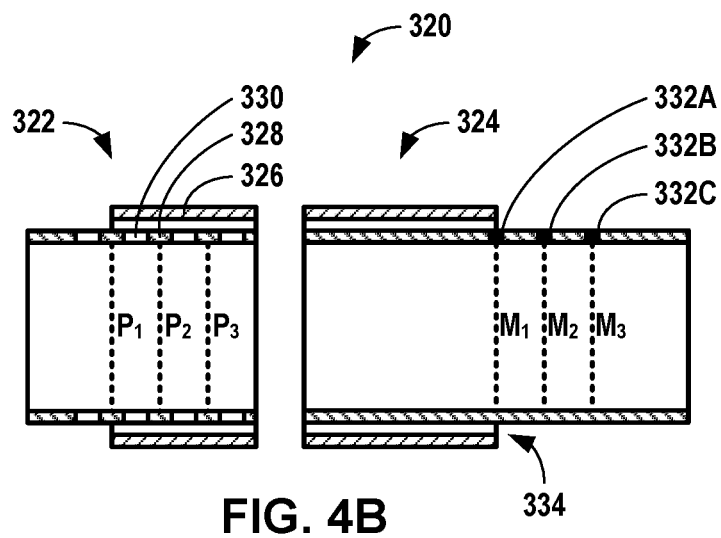
FIG. 4B is a schematic longitudinal cross-sectional diagram illustrating an example aspiration catheter system that includes an alignment element including a plurality of visible markers on an inner catheter.
Figure 4C:
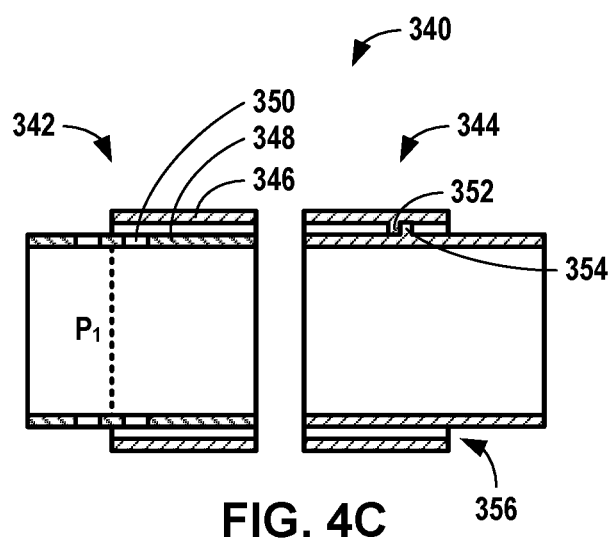
FIG. 4C is a schematic longitudinal cross-sectional diagram illustrating an example aspiration catheter system that includes an alignment element including one or more alignment structures.

The alignment elements discussed herein may have a variety of configurations. FIGS. 4A-4C are schematic longitudinal cross-sectional diagrams illustrating example aspiration catheter systems 300, 320, 340 having various example alignment elements for positioning an inner catheter at one or more predetermined positions within an outer catheter. Each aspiration catheter system 300, 320, 340 may be functionally similar to, for example, aspiration catheter system 10 of FIGS. 1A-1C.

FIG. 4A is a schematic longitudinal cross-sectional diagram illustrating example aspiration catheter system 300 that includes visible markers as an alignment element. Aspiration catheter system 300 includes an outer catheter 306, an inner catheter 308 within outer catheter 306, a plurality of sidewall openings 310 at a distal portion 302 of aspiration catheter system 300, and an alignment element at a proximal portion 304 of aspiration catheter system 300, the alignment element including an inner catheter visible marker 312 on inner catheter 308. When inner catheter visible marker 312 is aligned with an outer catheter proximal opening 314 of outer catheter 306, inner catheter 308 may be at the predetermined position P1 relative to outer catheter 306. In this way, a clinician operating aspiration catheter system 300 may adjust aspiration catheter system 300, such as by operating a proximal portion of inner catheter 308, using an easy to view visual indication. While visible marker 312 is described at proximal portion 304, in some examples, visible marker 312 may be located at other locations, such that a clinician may more easily observe a relationship between visual marker 312 and outer catheter proximal opening 314. In other examples, outer catheter 306 may include a visual marker, such that visual marker 312 may be aligned with the outer catheter visual marker.

FIG. 4B is a schematic longitudinal cross-sectional diagram illustrating example aspiration catheter system 320 that includes an alignment element including a plurality of visible markers. Aspiration catheter system 320 includes an outer catheter 326, an inner catheter 328 within outer catheter 326, a plurality of sidewall openings 330 at a distal portion 322 of aspiration catheter system 320, and an alignment element at a proximal portion 324 of aspiration catheter system 320 that includes three inner catheter visible marker 332A, 332B, 332C on inner catheter 328. Each marker 332A, 332B, 332C corresponds to a respective predetermined position $P_1$, $P_2$, $P_3$ of at least one sidewall opening of the plurality of sidewall openings of the inner catheter relative to the outer catheter distal opening when the respective marker 332 is at a respective marker position $M_1$, $M_2$, $M_3$ aligned with an outer catheter proximal opening 334 (or, alternatively, a visual marker on outer catheter 326). When outer catheter proximal opening 334 is aligned with a respective inner catheter visible marker 332A, 332B, 332C, aspiration catheter system 320 may be at the respective predetermined position $P_1$, $P_2$, $P_3$. For example, each predetermined position may have certain flow characteristics due to the proportion of sidewall openings 330 that are distal to the distal opening of outer catheter 326 (compared to the total number of sidewall openings 330 (including those within the outer catheter lumen 316)). In this way, a clinician operating aspiration catheter system 300 may adjust aspiration catheter system 300 using an easy to view visual indication to a variety of different predetermined positions.

FIG. 4C is a schematic longitudinal cross-sectional diagram illustrating example aspiration catheter system 340 that includes an alignment element including alignment structures. Aspiration catheter system 340 includes an outer catheter 346, an inner catheter 348 within outer catheter 346, a plurality of sidewall openings 350 at a distal portion 342 of aspiration catheter system 340, and an alignment element at a proximal portion 344 of aspiration catheter system 340, the alignment element including an inner catheter alignment structure 354 extending from an outer surface of inner catheter 348 and an outer catheter alignment structure 352 extending from an inner surface of outer catheter 346. Inner catheter alignment structure 354 may configured to engage with outer catheter alignment structure 352.

When inner catheter alignment structure 354 and outer catheter alignment structure 352 are engaged, inner catheter 348 may be at the predetermined position $P_1$ relative to outer catheter 346. In this way, a clinician operating aspiration catheter system 300 may adjust aspiration catheter system 300 and determine sidewall openings 350 are positioned at the desired location relative to the outer catheter distal opening without having to divert her gaze to observe a relative position of inner catheter 348 and outer catheter 346. While alignment structures 352, 354 are shown at proximal end 344, in some examples, alignment structures 353, 354 may be located at other locations. While alignment structures 352, 354 are shown as interlocking structures, in other examples, the alignments structures may include other mechanisms that limit travel of inner catheter 348 within outer catheter 346, such as a single structure at a proximal portion of inner catheter 346 that interacts with an edge of an outer catheter proximal opening 356 of outer catheter 346.

Figure 5:
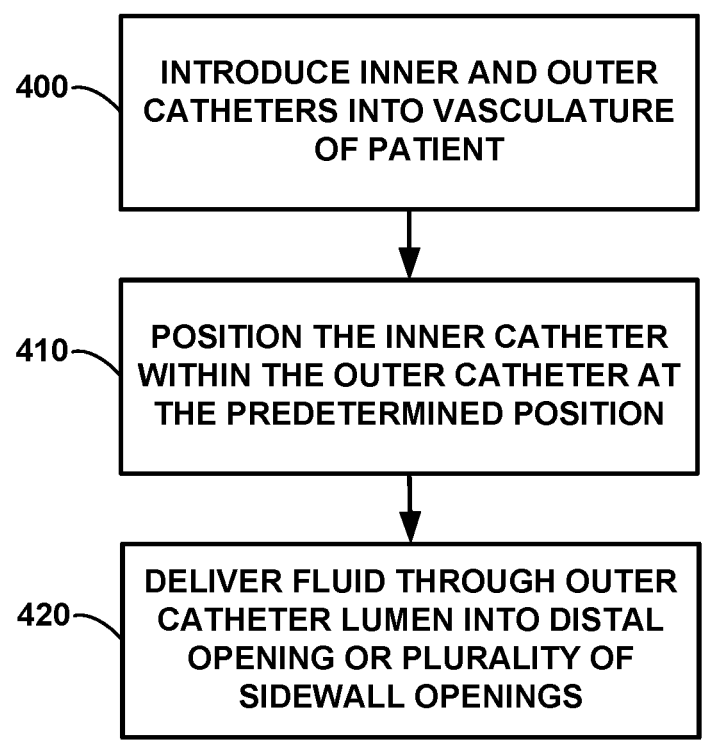
FIG. 5 is a flow diagram of an example method of using an aspiration catheter system that includes an outer catheter and an inner catheter configured to maintain suction and continuous flow of fluid on an engaged thrombus.

FIG. 5 is a flow diagram of an example method of using an aspiration catheter system that includes an outer catheter and an inner catheter configured to maintain suction and continuous flow of fluid on an engaged thrombus. The techniques of FIG. 5 are described with reference to the various aspects of aspiration system 2 of FIGS. 1A-1C for illustrative purposes; however, such descriptions are not intended to be limiting, and the techniques of FIG. 5 may be used with other examples of the aspiration systems disclosed herein, or otherwise. The technique of FIG. 5 includes introducing aspiration catheter system 10 into vasculature of a patient (400), positioning inner catheter 14 within outer catheter 12 at a predetermined position (410), and delivering a fluid through outer catheter lumen 16 into outer catheter distal opening 18 and/or a sidewall opening 24 of inner catheter 14 (420), thereby maintaining suction and continuous flow of fluid on an engaged thrombus. In some examples, the techniques described herein include removing aspiration catheter system 10 from the vasculature of the patient once the procedure is complete.

In some examples, introducing at least a portion of outer catheter 12 and inner catheter 14 into vasculature of a patient (400) may be aided by initially introducing a guidewire, guide catheter or another guide member into the vasculature of the patient to a target treatment site. In some examples, outer catheter 12 is a guide catheter that is initially introduced into the vasculature of the patient, e.g., over a guidewire and advanced to the target treatment site. Inner catheter 14 may then be introduced through an inner lumen of the guide catheter. In other examples, outer catheter 12 and inner catheter 14 may be navigated to a target treatment site inside of a separate guide catheter.

In some examples, aspiration catheter system 10 is inserted into vasculature of the patient prior to attachment of a remainder of aspiration system 2, while in other examples, aspiration catheter system 10 may be inserted into vasculature of the patient with a remainder of aspiration system 2 already attached, such as through aspiration tubing 8.

The technique of FIG. 5 may include various steps for initiating aspiration to remove a thrombus. For example, a distal end of aspiration catheter system 10 may be introduced into an intracranial blood vessel (or other blood vessel) and positioned so that inner catheter distal opening 22 is adjacent to and/or proximal of a thrombus. Once inner catheter distal opening 22 is positioned at a position corresponding to an estimated location of the thrombus, a clinician may deliver a fluid through outer catheter lumen 16. For example, a clinician operating aspiration system 2 may operate aspiration pump 6 to generate a positive pressure in outer catheter lumen 16 and a negative pressure in inner catheter lumen 20.

The technique of FIG. 5 can include positioning inner catheter 14 within outer catheter lumen 16 at the predetermined position $P_1$ such that at least one sidewall opening of the plurality of sidewall openings 24 remains positioned within outer catheter lumen 16 and at least one other sidewall opening of the plurality of sidewall openings 24 is positioned distal to outer catheter distal opening 18. For example, the clinician may adjust inner catheter 14 within outer catheter 12 until alignment element 26 indicates the predetermined position $P_1$.

In some examples, the technique of FIG. 5 may include positioning inner catheter distal opening 22 proximate to the thrombus in the vasculature so that the thrombus substantially covers inner catheter distal opening 22. In response to the thrombus substantially covering inner catheter distal opening 22, the fluid may be delivered through the at least one sidewall opening 24 into inner catheter lumen 20. In some examples, the fluid is delivered through outer catheter lumen 16 through the at least one sidewall opening 24 into inner catheter lumen 20 in response to a differential pressure between outer catheter lumen 16 and inner catheter lumen 20 being greater than or equal to a predetermined threshold value.

At least a portion of the fluid entering inner catheter lumen 20 through the at least one sidewall opening 24 may contact a surface of the thrombus. This continuous flow of fluid on the thrombus may cause loose particles to be removed from the surface of the thrombus. For example, the continuous flow of fluid may be relatively turbulent, such that the flow of fluid may exert an impacting force on the thrombus. Additionally, a suction from inner catheter lumen 20 may draw fluid from the surface of the thrombus and remove the fluid through inner catheter lumen 20.

In some examples, a clinician operating aspiration system 2 may adjust aspiration catheter system 10 to a second predetermined position corresponding to a different configuration of the plurality of sidewall openings 24 outside outer catheter lumen 16 (e.g., distal of distal opening 18) and within outer catheter lumen 16 (e.g., proximal of distal opening 18). For example, the clinician may desire that a higher flow rate of aspiration fluid passes through sidewall openings 24 that are distal of outer catheter distal opening 18; in such a case, the clinician may select a predetermined position corresponding to an increased number of sidewall openings proximal of catheter distal opening 18 (e.g., within lumen 16).

As pieces of the thrombus are removed, the thrombus may block inner catheter distal opening 22 to a lesser extent, such that flow of fluid into inner catheter distal opening 22 may increase. In response, the clinician may reposition aspiration catheter system 10, such as by advancing aspiration catheter system in a distal direction, to continue to remove the thrombus.

Catheter 12 may be removed from the vasculature once the procedure is complete.

In some examples, inner catheter 14 may be used during a medical procedure with all of sidewall openings 24 in a blood vessel of a patient distal to or otherwise not within outer catheter 12 or another outer catheter. For example, inner catheter 14 may be used on its own without outer catheter 12, although a guide catheter may be used to deliver inner catheter 14 to a treatment site within the vasculature of a patient. In some of these examples, inner catheter 14 may be used as an aspiration catheter. For example, aspiration pump 6 may create a negative pressure on inner catheter 14 to draw fluid into inner catheter lumen 20, e.g. to aspirate a thrombus from a blood vessel. In some of these examples, sidewall openings 24 may be configured to enable flow of fluid from the blood vessel into inner catheter lumen 20 through sidewall openings 24, such as in response to a positive pressure in the blood vessel being greater than a negative pressure in inner catheter lumen 20. In some examples, the plurality of sidewall openings 24 may be configured to open in response to a differential pressure in the blood vessel and in inner catheter lumen 20 (i.e., a difference between a positive pressure in the blood vessel and a negative pressure in inner catheter lumen 20) being greater than or equal to a predetermined differential pressure threshold value. This may enable fluid to flow into inner catheter lumen 20 when inner catheter distal opening 22 is blocked, such as by the thrombus. In this way, the clinician may maintain both suction on an engaged thrombus and continuous flow of fluid on the engaged thrombus, which may result in more effective removal of the thrombus from the vasculature of the patient.

Various aspects of the disclosure have been described. These and other aspects are within the scope of the following claims. While the dimensions of catheters described above primarily refer to diameters, in other examples, the catheters described herein may have cross-sectional shapes (the cross-section being taken in a direction orthogonal to a longitudinal axis of the respective catheter) other than circular. In these examples, the inner and outer catheters of an aspiration catheter system may have the same relative configuration (e.g., the inner catheter being configured to be received in an inner lumen of the outer catheter) and same functions described above with respect to catheters having circular cross-sections.

What is claimed is:

1. An aspiration catheter system comprising:
   an outer catheter configured to be navigated within vasculature of a patient from an entry site to a target site, the outer catheter defining an outer catheter lumen, and an outer catheter distal opening;
   an inner catheter configured to be positioned within the outer catheter lumen, the inner catheter defining an inner catheter lumen, an inner catheter distal opening, and a plurality of sidewall openings proximal to the inner catheter distal opening; and
   an alignment element configured to indicate a predetermined position of the inner catheter relative to the outer catheter when the inner catheter is received within the outer catheter lumen,
   wherein when the inner catheter is at the predetermined position, at least one sidewall opening of the plurality of sidewall openings remains positioned within the outer catheter lumen and at least one other sidewall opening of the plurality of sidewall openings is positioned distal to the outer catheter distal opening, and
   wherein the outer catheter is configured to fluidically couple the outer catheter lumen to a fluid circulation system.

2. The aspiration catheter system of claim 1, wherein the alignment element comprises a visible marker on the inner catheter.

3. The aspiration catheter system of claim 1, wherein the alignment element comprises an alignment structure extending from the inner catheter and configured to engage with a proximal end of the outer catheter.

4. The aspiration catheter system of claim 1, wherein the alignment element comprises a plurality of markers, each marker corresponding to a predetermined position of at least one sidewall opening of the plurality of sidewall openings of the inner catheter relative to the outer catheter distal opening.

5. The aspiration catheter system of claim 1, wherein an inner circumference of the outer catheter is between about 50 microns and about 200 microns greater than an outer circumference of the inner catheter.

6. The aspiration catheter system of claim 1, wherein at least one sidewall opening of the plurality of sidewall openings comprises a one-way valve configured to permit flow of fluid into the inner catheter lumen.

7. The aspiration catheter system of claim 6, wherein the one-way valve is configured to open in response to a differential pressure between the outer catheter lumen and the inner catheter lumen being greater than or equal to a predetermined threshold value.

8. The aspiration catheter system of claim 6, wherein the one-way valve comprises a duckbill valve, a slit valve, or a flexible flap positioned at the respective sidewall openings.

9. The aspiration catheter system of claim 1, wherein the distal-most sidewall opening of the plurality of sidewall openings is positioned between about 0.5 centimeters and about 10 centimeters proximal to the inner catheter distal opening.

10. The aspiration catheter system of claim 1, further comprising:
    the fluid circulation system coupled to a proximal portion of the outer catheter and a proximal portion of the inner catheter,
    wherein the fluid circulation system is configured to deliver fluid through the outer catheter lumen and receive fluid through the inner catheter lumen.

11. The aspiration catheter system of claim 1, wherein the sidewall openings of the plurality of sidewall openings are circumferentially distributed around an outer perimeter of the inner catheter.

12. The aspiration catheter system of claim 1, wherein the sidewall openings of the plurality of sidewall openings are distributed axially along the inner catheter.

13. The aspiration catheter system of claim 1,
    wherein the outer catheter defines an outer catheter proximal opening,
    wherein the inner catheter defines an inner catheter proximal opening, and
    wherein, when the inner catheter is at the predetermined position:
        the outer catheter proximal opening is configured to receive aspiration fluid into the outer catheter lumen between the outer catheter and the inner catheter, and
        the inner catheter proximal opening is configured to discharge aspiration fluid from the inner catheter lumen.

14. The aspiration catheter system of claim 1, wherein the outer catheter is configured to be navigated within cranial vasculature of the patient.

15. A method, comprising:
    introducing at least a portion of an outer catheter and an inner catheter of an aspiration catheter system into vasculature of a patient, the aspiration catheter system comprising:
        the outer catheter defining an outer catheter lumen and an outer catheter distal opening;
        the inner catheter defining an inner catheter lumen, an inner catheter distal opening, and a plurality of sidewall openings proximal to the inner catheter distal opening; and
        an alignment element configured to indicate a predetermined position of the inner catheter relative to the outer catheter when the inner catheter is received within the outer catheter distal opening;
    positioning the inner catheter within the outer catheter lumen at the predetermined position such that at least one sidewall opening of the plurality of sidewall openings remains positioned within the outer catheter lumen and at least one other sidewall opening of the plurality of sidewall openings is positioned distal to the outer catheter distal opening; and delivering a fluid through the outer catheter lumen and through at least one of:
- the outer catheter distal opening into the vasculature of the patient, or
- at least one sidewall opening of the plurality of sidewall openings into the inner catheter lumen.

16. The method of claim 15, wherein the fluid is delivered through the outer catheter lumen through the at least one sidewall opening into the inner catheter lumen in response to a differential pressure between the outer catheter lumen and the inner catheter lumen being greater than or equal to a predetermined threshold value.

17. The method of claim 15, further comprising:
positioning the inner catheter distal opening proximate to a soft tissue in the vasculature; and
generating a suction in the inner catheter lumen.

18. The method of claim 17,
wherein the inner catheter distal opening is positioned in the vasculature so that the soft tissue substantially covers the inner catheter distal opening, and
wherein the fluid is delivered through the at least one sidewall opening in response to the soft tissue substantially covering the inner catheter distal opening.

19. The method of claim 15, wherein the alignment element comprises an alignment structure extending from the inner catheter and configured to engage with a proximal end of the outer catheter.

20. The method of claim 15, wherein the alignment element comprises a plurality of markings, each marking corresponding to a predetermined position of at least one sidewall opening of the plurality of sidewall openings of the inner catheter relative to the outer catheter distal opening.

21. An aspiration catheter system comprising:
an outer catheter configured to be navigated within vasculature of a patient from an entry site to a target site, the outer catheter defining an outer catheter lumen and an outer catheter distal opening;
an inner catheter configured to be positioned within the outer catheter lumen, the inner catheter defining an inner catheter lumen, an inner catheter distal opening, and a plurality of sidewall openings proximal to the inner catheter distal opening; and
an alignment element configured to indicate a predetermined position of the inner catheter relative to the outer catheter when the inner catheter is received within the outer catheter lumen,
wherein when the inner catheter is at the predetermined position, the aspiration catheter system defines:
a first flow path of fluid from the outer catheter lumen through the outer catheter distal opening and the inner catheter distal opening to the inner catheter lumen,
a second flow path of the fluid from the outer catheter lumen through the outer catheter distal opening and at least a first sidewall opening of the plurality of sidewall openings to the inner catheter lumen, and
a third flow path of the fluid from the outer catheter lumen directly through at least a second sidewall opening of the plurality of sidewall openings to the inner catheter lumen, and
wherein the outer catheter is configured to fluidically couple the outer catheter lumen to a fluid circulation system.

22. The aspiration catheter system of claim 21, further comprising the fluid circulation system, the fluid circulation system including an aspiration pump fluidically coupled to a proximal portion of the outer catheter and a proximal portion of the inner catheter, the aspiration pump configured to:
deliver an aspiration fluid to the outer catheter lumen;
generate a positive pressure on the outer catheter lumen; and
generate a negative pressure on the inner catheter lumen.

23. The aspiration catheter system of claim 22, wherein when the inner catheter distal opening is at least partially blocked, the aspiration catheter system is configured to deliver the fluid from the outer catheter lumen to the inner catheter lumen through at least one of the second flow path or the third flow path.

* * * * *